United States Patent [19]

Celeste et al.

[11] Patent Number: 5,637,480

[45] Date of Patent: Jun. 10, 1997

[54] DNA MOLECULES ENCODING BONE MORPHOGENETIC PROTEIN-10

[75] Inventors: Anthony J. Celeste; John M. Wozney, both of Hudson, Mass.

[73] Assignee: Genetics Institute, Inc., Cambridge, Mass.

[21] Appl. No.: 247,908

[22] Filed: May 20, 1994

Related U.S. Application Data

[63] Continuation-in-part of Ser. No. 61,695, May 12, 1993, abandoned.

[30] Foreign Application Priority Data

May 12, 1994 [WO] WIPO ............... PCT/US94/05288

[51] Int. Cl.$^6$ ............... C07K 14/51; C12N 15/16; C12N 15/85
[52] U.S. Cl. ............... 435/69.4; 435/252.3; 435/320.1; 435/325; 435/360; 435/364; 435/365.1; 536/23.4; 536/23.51; 530/399; 930/10
[58] Field of Search ............... 536/23.4, 23.51; 435/240.2, 320.1, 69.4, 252.3; 514/12; 530/399; 424/484, 486

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,526 | 6/1984 | Urist | 530/350 |
| 4,563,350 | 1/1986 | Nathan | 424/95 |
| 4,627,982 | 12/1986 | Seyedin et al. | 424/95 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,804,744 | 2/1989 | Sen | 530/350 |
| 4,968,590 | 11/1990 | Kuberasampath et al. | 530/326 |
| 5,013,649 | 5/1991 | Wang et al. | 435/69 |
| 5,106,748 | 4/1992 | Wozney et al. | 435/252.3 |
| 5,187,076 | 2/1993 | Wozney et al. | 435/69 |

FOREIGN PATENT DOCUMENTS

| | | |
|---|---|---|
| 2 017466 | 5/1990 | Canada . |
| 33 6760 A2 | 6/1989 | European Pat. Off. . |
| 4 165 78A2 | 5/1990 | European Pat. Off. . |
| 4 094 72 A1 | 11/1990 | European Pat. Off. . |
| WO91/18047 | 11/1991 | WIPO . |

OTHER PUBLICATIONS

Wozney et al "Growth Factors Influencing Bone Development" *J. Cell Sci. Suppl.* 13:149–156 (1990).
Burt, "Evolutionary Grouping of the Transforming Growth Factor–β Superfamily", *BBRC* 184(2): 590–595 (Apr. 1992).
Wozney, Molecular Reproduction and Development 32:160–167(1992).
Urist et al., Science 220:680–686 (1983).
Luyten et al., J. Biol. Chem. 264(23):13377–13380 (1989).
Sampath et al., PNAS 84:7109–7113 (1987).
Ozkaynak et al., EMBO J. 9(7):2085–2093 (1990).
Wozney, Progress in Growth Factor Research, 1:267–280 (1989).

*Primary Examiner*—Stephen G. Walsh
*Attorney, Agent, or Firm*—Steven R. Lazar; Thomas J. DesRosier

[57] ABSTRACT

Purified Bone Morphogenetic Protein-10 proteins and processes for producing them are disclosed. Recombinant DNA molecules encoding the BMP-10 proteins are also disclosed. The proteins may be used in the treatment of bone and cartilage defects and in wound healing and related tissue repair.

17 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1442 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bos taurus
        ( B ) STRAIN: bovine BMP-10

( i x ) FEATURE:
        ( A ) NAME/KEY: CDS
        ( B ) LOCATION: 167..1105

( i x ) FEATURE:
        ( A ) NAME/KEY: misc_feature
        ( B ) LOCATION: 165..778
        ( D ) OTHER INFORMATION: /note="partial coding sequence for propeptide"

( i x ) FEATURE:
        ( A ) NAME/KEY: mat_peptide
        ( B ) LOCATION: 779..1102
        ( D ) OTHER INFORMATION: /note="beginning of mature peptide"

( i x ) FEATURE:
        ( A ) NAME/KEY: misc_feature
        ( B ) LOCATION: 163..164
        ( D ) OTHER INFORMATION: /note="3'end of intron"

(ix) FEATURE:
    (A) NAME/KEY: misc_feature
    (B) LOCATION: 165..166
    (D) OTHER INFORMATION: /note="the last two-thirds of a codon which is interrupted by an intron"

(xi) SEQUENCE DESCRIPTION: SEQ ID NO:1:

```
TTCGGTACTT CCTCTTAGAG AATGCCAACA CTGTGTTTGT TTTCACTGAT TTTCCTTCAT      60

TCTTTCTGTG TGGAGAGAAT GGACAGGCAC TCTTATTGCA TAAATAAGCA TCTGTTTTCC     120

TCTGCTACAT GCTGCAAATC TGATTTCTTT TTTGTTTTTT CCAGAT CTG TTT TCC        175
                                                 Leu Phe Ser
                                                    -204

CAA CCA GCC AGT TTT AAT GGA CTC CGA AAA TAC CCT CTC CTC TTC AAC        223
Gln Pro Ala Ser Phe Asn Gly Leu Arg Lys Tyr Pro Leu Leu Phe Asn
    -200            -195                -190

GTA TCC ATC CCT CAC CAT GAA GAC ATC ATC ATG GCT GAG CTC AGG TTG        271
Val Ser Ile Pro His His Glu Asp Ile Ile Met Ala Glu Leu Arg Leu
-185             -180                -175             -170

TAC ACC CTG GTG CAA AGA GAC CGC CTT ATA TAT GAA GGA GTG GAC CGA        319
Tyr Thr Leu Val Gln Arg Asp Arg Leu Ile Tyr Glu Gly Val Asp Arg
                 -165                -160                -155

AAA ATC ACC ATT TTT GAA GTA CTT GAG AGC AAA GAG GAC CAT GAA GGG        367
Lys Ile Thr Ile Phe Glu Val Leu Glu Ser Lys Glu Asp His Glu Gly
             -150                -145                -140

GAA AGA AAC ATG CTG GTC TTG GTG TCA GGG GAG ATC TAC GGA ACC AAC        415
Glu Arg Asn Met Leu Val Leu Val Ser Gly Glu Ile Tyr Gly Thr Asn
             -135                -130                -125

AGT GAG TGG GAG ACT TTT GAT GTC ACT GAT GCC ATC AGG CAT TGG CAA        463
Ser Glu Trp Glu Thr Phe Asp Val Thr Asp Ala Ile Arg His Trp Gln
    -120                -115                -110

AAG TCA GGC TCA TCC ACC CAC CAG CTG GAG GTC CAC ATT GAG AGC AAA        511
Lys Ser Gly Ser Ser Thr His Gln Leu Glu Val His Ile Glu Ser Lys
-105                -100                 -95                 -90

CAC GAA ATG GAG GAC ACA CTT GGC AGG GGA CAG CTG GAA ATA GAC ACT        559
His Glu Met Glu Asp Thr Leu Gly Arg Gly Gln Leu Glu Ile Asp Thr
                 -85                 -80                  -75

AGT GCC CGG AAT AAG CAC GAT CCT TTG CTT GTC GTG TTT TCT GAT GAC        607
Ser Ala Arg Asn Lys His Asp Pro Leu Leu Val Val Phe Ser Asp Asp
            -70                  -65                  -60

CAA AGC AGT GAG AAG GAG CGG AAA GAG GAA CTG GAT GAA ATG ATC GCC        655
Gln Ser Ser Glu Lys Glu Arg Lys Glu Glu Leu Asp Glu Met Ile Ala
        -55                  -50                  -45

CAC GAG CAA TTC CCA GAG ATG GAC AAC CTG GAT TTG GAC GGT TAT TCC        703
His Glu Gln Phe Pro Glu Met Asp Asn Leu Asp Leu Asp Gly Tyr Ser
    -40                  -35                  -30

AAC GGA CCT GGG GAA GAG GCT TTG CTG CAG ATG AGG TCG AAT ATC ATC        751
Asn Gly Pro Gly Glu Glu Ala Leu Leu Gln Met Arg Ser Asn Ile Ile
-25                  -20                  -15                  -10

TAT GAC TCC ACT GCC CGC ATC AGA AGG AAT GCA AAA GGA AAC TAC TGC        799
Tyr Asp Ser Thr Ala Arg Ile Arg Arg Asn Ala Lys Gly Asn Tyr Cys
                  -5                   1                   5

AAG AGG ACC CCG CTC TAC ATC GAC TTC AAG GAG ATT GGC TGG GAC TCT        847
Lys Arg Thr Pro Leu Tyr Ile Asp Phe Lys Glu Ile Gly Trp Asp Ser
         10                  15                  20

TGG ATC ATC GCT CCA CCT GGA TAT GAA GCC TAT GAA TGT CGT GGT GTT        895
Trp Ile Ile Ala Pro Pro Gly Tyr Glu Ala Tyr Glu Cys Arg Gly Val
         25                  30                  35

TGC AAC TAC CCC CTG GCA GAG CAT CTC ACC CCC ACA AAG CAT GCG ATT        943
Cys Asn Tyr Pro Leu Ala Glu His Leu Thr Pro Thr Lys His Ala Ile
 40                  45                  50                  55
```

| | | | | | | | | | | | | | | | | |
|---|---|---|---|---|---|---|---|---|---|---|---|---|---|---|---|---|
|ATC|CAG|GCC|TTG|GTC|CAC|CTC|AAG|AAT|TCC|CAG|AAG|GCT|TCC|AAA|GCC|991|
|Ile|Gln|Ala|Leu|Val|His|Leu|Lys|Asn|Ser|Gln|Lys|Ala|Ser|Lys|Ala| |
| | | | |60| | | |65| | | |70| | | | |
|TGC|TGT|GTG|CCC|ACC|AAG|CTC|GAG|CCC|ATC|TCC|ATC|CTC|TAT|TTA|GAT|1039|
|Cys|Cys|Val|Pro|Thr|Lys|Leu|Glu|Pro|Ile|Ser|Ile|Leu|Tyr|Leu|Asp| |
| | | |75| | | |80| | | |85| | | | | |
|AAG|GGC|GTC|GTC|ACC|TAC|AAG|TTT|AAA|TAT|GAG|GGC|ATG|GCT|GTC|TCT|1087|
|Lys|Gly|Val|Val|Thr|Tyr|Lys|Phe|Lys|Tyr|Glu|Gly|Met|Ala|Val|Ser| |
| | |90| | | |95| | | |100| | | | | | |
|GAA|TGT|GGC|TGT|AGA|TAGGAGAGGA|ATCCTGTGGC|TTATTTAATA|ACTGTAAATG| | | | | | | |1142|
|Glu|Cys|Gly|Cys|Arg| | | | | | | | | | | | |
| |105| | | | | | | | | | | | | | | |

| | | | | |
|---|---|---|---|---|
|TGTATATTTT|GTGTTCCTAT|TTAATGAGAT|TATTTAATAA|GGGTGTACAG|ATCATAGAGG|1202|
|CTTGCTGCCT|TAGGGAATTT|GACAGGTCGG|TTTGTTGTAG|GAAATCCATG|TTTTACTCTA|1262|
|CAGTCGAGTC|CCTTCCAATC|TATTTTTCTT|TGGACTTACC|ATGTCCTGCA|ATGCCATCTC|1322|
|TAACAGCAAG|GCAAGCCCAC|ACTACTTGCC|TTCTATGTCA|ATTCAAAAGG|AACACCGCTA|1382|
|AGCAGAAATA|CAGTGTCAGG|AGAGGTAGAT|ATTTGTGTAT|GTATATGTGT|ACATAGATAA|1442|

( 2 ) INFORMATION FOR SEQ ID NO:2:

( i ) SEQUENCE CHARACTERISTICS:
        ( A ) LENGTH: 312 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Leu|Phe|Ser|Gln|Pro|Ala|Ser|Phe|Asn|Gly|Leu|Arg|Lys|Tyr|Pro|Leu|
|-204| | | |-200| | | |-195| | | |-190| | |
|Leu|Phe|Asn|Val|Ser|Ile|Pro|His|His|Glu|Asp|Ile|Ile|Met|Ala|Glu|
| | | |-185| | | |-180| | | |-175| | | |
|Leu|Arg|Leu|Tyr|Thr|Leu|Val|Gln|Arg|Asp|Arg|Leu|Ile|Tyr|Glu|Gly|
| | |-170| | | |-165| | | |-160| | | | |
|Val|Asp|Arg|Lys|Ile|Thr|Ile|Phe|Glu|Val|Leu|Glu|Ser|Lys|Glu|Asp|
| |-155| | | |-150| | | |-145| | | | | |
|His|Glu|Gly|Glu|Arg|Asn|Met|Leu|Val|Leu|Val|Ser|Gly|Glu|Ile|Tyr|
|-140| | | |-135| | | |-130| | | |-125| | |
|Gly|Thr|Asn|Ser|Glu|Trp|Glu|Thr|Phe|Asp|Val|Thr|Asp|Ala|Ile|Arg|
| | | |-120| | | |-115| | | |-110| | | |
|His|Trp|Gln|Lys|Ser|Gly|Ser|Ser|Thr|His|Gln|Leu|Glu|Val|His|Ile|
| | |-105| | | |-100| | | |-95| | | | |
|Glu|Ser|Lys|His|Glu|Met|Glu|Asp|Thr|Leu|Gly|Arg|Gly|Gln|Leu|Glu|
| |-90| | | |-85| | | |-80| | | | | |
|Ile|Asp|Thr|Ser|Ala|Arg|Asn|Lys|His|Asp|Pro|Leu|Leu|Val|Val|Phe|
|-75| | | |-70| | | |-65| | | | | | |
|Ser|Asp|Asp|Gln|Ser|Ser|Glu|Lys|Glu|Arg|Lys|Glu|Glu|Leu|Asp|Glu|
|-60| | | |-55| | | |-50| | | |-45| | |
|Met|Ile|Ala|His|Glu|Gln|Phe|Pro|Glu|Met|Asp|Asn|Leu|Asp|Leu|Asp|
| | | |-40| | | |-35| | | |-30| | | |
|Gly|Tyr|Ser|Asn|Gly|Pro|Gly|Glu|Glu|Ala|Leu|Leu|Gln|Met|Arg|Ser|
| | |-25| | | |-20| | | |-15| | | | |
|Asn|Ile|Ile|Tyr|Asp|Ser|Thr|Ala|Arg|Ile|Arg|Arg|Asn|Ala|Lys|Gly|
| | |-10| | | |-5| | | |1| | | | |
|Asn|Tyr|Cys|Lys|Arg|Thr|Pro|Leu|Tyr|Ile|Asp|Phe|Lys|Glu|Ile|Gly|
|5| | | |10| | | |15| | | |20| | |

```
Trp  Asp  Ser  Trp  Ile  Ile  Ala  Pro  Pro  Gly  Tyr  Glu  Ala  Tyr  Glu  Cys
               25                       30                       35

Arg  Gly  Val  Cys  Asn  Tyr  Pro  Leu  Ala  Glu  His  Leu  Thr  Pro  Thr  Lys
               40                       45                       50

His  Ala  Ile  Ile  Gln  Ala  Leu  Val  His  Leu  Lys  Asn  Ser  Gln  Lys  Ala
               55                       60                       65

Ser  Lys  Ala  Cys  Cys  Val  Pro  Thr  Lys  Leu  Glu  Pro  Ile  Ser  Ile  Leu
      70                       75                       80

Tyr  Leu  Asp  Lys  Gly  Val  Val  Thr  Tyr  Lys  Phe  Lys  Tyr  Glu  Gly  Met
 85                       90                       95                      100

Ala  Val  Ser  Glu  Cys  Gly  Cys  Arg
                105
```

( 2 ) INFORMATION FOR SEQ ID NO:3:

( i ) SEQUENCE CHARACTERISTICS:
        ( A ) LENGTH: 197 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( B ) STRAIN: Human BMP-10

( i x ) FEATURE:
        ( A ) NAME/KEY: CDS
        ( B ) LOCATION: 30..167

( x i ) SEQUENCE DESCRIPTION: SEQ ID NO:3:

```
TCTAGACCTA  TGAATGTCGT  GGTGTTTGC  AAC  TAC  CCC  CTG  GCA  GAG  CAT  CTC           53
                                   Asn  Tyr  Pro  Leu  Ala  Glu  His  Leu
                                    1                  5

ACA  CCC  ACA  AAG  CAT  GCA  ATT  ATC  CAG  GCC  TTG  GTC  CAC  CTC  AAG  AAT     101
Thr  Pro  Thr  Lys  His  Ala  Ile  Ile  Gln  Ala  Leu  Val  His  Leu  Lys  Asn
      10                       15                       20

TCC  CAG  AAA  GCT  TCC  AAA  GCC  TGC  TGT  GTG  CCC  ACA  AAG  CTA  GAG  CCC     149
Ser  Gln  Lys  Ala  Ser  Lys  Ala  Cys  Cys  Val  Pro  Thr  Lys  Leu  Glu  Pro
 25                       30                       35                       40

ATC  TCC  ATC  CTC  TAT  TTA  GATAAGGGCG  TCGTCACCTA  CAAGGGATCC                   197
Ile  Ser  Ile  Leu  Tyr  Leu
                45
```

( 2 ) INFORMATION FOR SEQ ID NO:4:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asn  Tyr  Pro  Leu  Ala  Glu  His  Leu  Thr  Pro  Thr  Lys  His  Ala  Ile  Ile
 1                       5                       10                       15

Gln  Ala  Leu  Val  His  Leu  Lys  Asn  Ser  Gln  Lys  Ala  Ser  Lys  Ala  Cys
               20                       25                       30

Cys  Val  Pro  Thr  Lys  Leu  Glu  Pro  Ile  Ser  Ile  Leu  Tyr  Leu
               35                       40                       45
```

( 2 ) INFORMATION FOR SEQ ID NO:5:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: primer A to bovine BMP-10

( x i ) SEQUENCE DESCRIPTION: SEQ ID NO:5:

TGCTCTAGAC CTATGAATGT CGTGGTGTTT GC    32

( 2 ) INFORMATION FOR SEQ ID NO:6:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: primer B to BMP-10

( x i ) SEQUENCE DESCRIPTION: SEQ ID NO:6:

TAGGGATCCC TTGTAGGTGA CGACGCCCTT ATC    33

( 2 ) INFORMATION FOR SEQ ID NO:7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: DNA inserted into pMT2 CXM ( x i ) SEQUENCE DESCRIPTION: SEQ ID NO:7:

CATGGGCAGC TCGAG    15

( 2 ) INFORMATION FOR SEQ ID NO:8:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: DNA inserted into pMT21

( i x ) FEATURE:
    ( A ) NAME/KEY: misc_feature
    ( B ) LOCATION: 1..6
    ( D ) OTHER INFORMATION: /note="PstI restriction site"

( i x ) FEATURE:
    ( A ) NAME/KEY: misc_feature
    ( B ) LOCATION: 15..26
    ( D ) OTHER INFORMATION: /note="Eco RI and XhoI restriction
        sites"

( x i ) SEQUENCE DESCRIPTION: SEQ ID NO:8:

CTGCAGGCGA GCCTGAATTC CTCGAGCCAT CATG    34

( 2 ) INFORMATION FOR SEQ ID NO:9:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Portion of the EMC virus leader sequence ( x ) PUBLICATION INFORMATION:
        ( A ) AUTHORS: Jung, S K
        ( C ) JOURNAL: J. Virol.
        ( D ) VOLUME: 63
        ( F ) PAGES: 1651-1660
        ( G ) DATE: 1989

( x i ) SEQUENCE DESCRIPTION: SEQ ID NO:9:

```
CGAGGTTAAA AAACGTCTAG GCCCCCCGAA CCACGGGGAC GTGGTTTTCC TTTGAAAAAC      60

ACGATTGC                                                               68
```

( 2 ) INFORMATION FOR SEQ ID NO:10:

( i ) SEQUENCE CHARACTERISTICS:
        ( A ) LENGTH: 1584 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human BMP-10

( v i i ) IMMEDIATE SOURCE:
        ( B ) CLONE: 20 GEN.3/HFL-3

( i x ) FEATURE:
        ( A ) NAME/KEY: CDS
        ( B ) LOCATION: 160..1431

( i x ) FEATURE:
        ( A ) NAME/KEY: sig_peptide
        ( B ) LOCATION: 160..1107

( i x ) FEATURE:
        ( A ) NAME/KEY: mat_peptide
        ( B ) LOCATION: 1108..1431

( x i ) SEQUENCE DESCRIPTION: SEQ ID NO:10:

```
GGGGAGAGGA AGAGTGGTAG GGGGAGGGAG AGAGAGAGGA AGAGTTTCCA AACTTGTCTC                60

CAGTGACAGG AGACATTTAC GTTCCACAAG ATAAAACTGC CACTTAGAGC CCAGGGAAGC               120

TAAACCTTCC TGGCTTGGCC TAGGAGCTCG AGCGGAGTC ATG GGC TCT CTG GTC                  174
                                            Met Gly Ser Leu Val
                                            -316 -315

CTG ACA CTG TGC GCT CTT TTC TGC CTG GCA GCT TAC TTG GTT TCT GGC                 222
Leu Thr Leu Cys Ala Leu Phe Cys Leu Ala Ala Tyr Leu Val Ser Gly
    -310              -305              -300

AGC CCC ATC ATG AAC CTA GAG CAG TCT CCT CTG GAA GAA GAT ATG TCC                 270
Ser Pro Ile Met Asn Leu Glu Gln Ser Pro Leu Glu Glu Asp Met Ser
-295              -290              -285              -280

CTC TTT GGT GAT GTT TTC TCA GAG CAA GAC GGT GTC GAC TTT AAC ACA                 318
Leu Phe Gly Asp Val Phe Ser Glu Gln Asp Gly Val Asp Phe Asn Thr
                  -275              -270              -265

CTG CTC CAG AGC ATG AAG GAT GAG TTT CTT AAG ACA CTA AAC CTC TCT                 366
Leu Leu Gln Ser Met Lys Asp Glu Phe Leu Lys Thr Leu Asn Leu Ser
```

| | | |
|---|---|---|
| GAC ATC CCC ACG CAG GAT TCA GCC AAG GTG GAC CCA CCA GAG TAC ATG<br>Asp Ile Pro Thr Gln Asp Ser Ala Lys Val Asp Pro Pro Glu Tyr Met<br>-245 -240 -235 | | 414 |
| TTG GAA CTC TAC AAC AAA TTT GCA ACA GAT CGG ACC TCC ATG CCC TCT<br>Leu Glu Leu Tyr Asn Lys Phe Ala Thr Asp Arg Thr Ser Met Pro Ser<br>-230 -225 -220 | | 462 |
| GCC AAC ATC ATT AGG AGT TTC AAG AAT GAA GAT CTG TTT TCC CAG CCG<br>Ala Asn Ile Ile Arg Ser Phe Lys Asn Glu Asp Leu Phe Ser Gln Pro<br>-215 -210 -205 -200 | | 510 |
| GTC AGT TTT AAT GGG CTC CGA AAA TAC CCC CTC CTC TTC AAT GTG TCC<br>Val Ser Phe Asn Gly Leu Arg Lys Tyr Pro Leu Leu Phe Asn Val Ser<br>-195 -190 -185 | | 558 |
| ATT CCT CAC CAT GAA GAG GTC ATC ATG GCT GAA CTT AGG CTA TAC ACA<br>Ile Pro His His Glu Glu Val Ile Met Ala Glu Leu Arg Leu Tyr Thr<br>-180 -175 -170 | | 606 |
| CTG GTG CAA AGG GAT CGT ATG ATA TAC GAT GGA GTA GAC CGG AAA ATT<br>Leu Val Gln Arg Asp Arg Met Ile Tyr Asp Gly Val Asp Arg Lys Ile<br>-165 -160 -155 | | 654 |
| ACC ATT TTT GAA GTG CTG GAG AGC AAA GGG GAT AAT GAG GGA GAA AGA<br>Thr Ile Phe Glu Val Leu Glu Ser Lys Gly Asp Asn Glu Gly Glu Arg<br>-150 -145 -140 | | 702 |
| AAC ATG CTG GTC TTG GTG TCT GGG GAG ATA TAT GGA ACC AAC AGT GAG<br>Asn Met Leu Val Leu Val Ser Gly Glu Ile Tyr Gly Thr Asn Ser Glu<br>-135 -130 -125 -120 | | 750 |
| TGG GAG ACT TTT GAT GTC ACA GAT GCC ATC AGA CGT TGG CAA AAG TCA<br>Trp Glu Thr Phe Asp Val Thr Asp Ala Ile Arg Arg Trp Gln Lys Ser<br>-115 -110 -105 | | 798 |
| GGC TCA TCC ACC CAC CAG CTG GAG GTC CAC ATT GAG AGC AAA CAC GAT<br>Gly Ser Ser Thr His Gln Leu Glu Val His Ile Glu Ser Lys His Asp<br>-100 -95 -90 | | 846 |
| GAA GCT GAG GAT GCC AGC AGT GGA CGG CTA GAA ATA GAT ACC AGT GCC<br>Glu Ala Glu Asp Ala Ser Ser Gly Arg Leu Glu Ile Asp Thr Ser Ala<br>-85 -80 -75 | | 894 |
| CAG AAT AAG CAT AAC CCT TTG CTC ATC GTG TTT TCT GAT GAC CAA AGC<br>Gln Asn Lys His Asn Pro Leu Leu Ile Val Phe Ser Asp Asp Gln Ser<br>-70 -65 -60 | | 942 |
| AGT GAC AAG GAG AGG AAG GAG GAA CTG AAT GAA ATG ATT TCC CAT GAG<br>Ser Asp Lys Glu Arg Lys Glu Glu Leu Asn Glu Met Ile Ser His Glu<br>-55 -50 -45 -40 | | 990 |
| CAA CTT CCA GAG CTG GAC AAC TTG GGC CTG GAT AGC TTT TCC AGT GGA<br>Gln Leu Pro Glu Leu Asp Asn Leu Gly Leu Asp Ser Phe Ser Ser Gly<br>-35 -30 -25 | | 1038 |
| CCT GGG GAA GAG GCT TTG TTG CAG ATG AGA TCA AAC ATC ATC TAT GAC<br>Pro Gly Glu Glu Ala Leu Leu Gln Met Arg Ser Asn Ile Ile Tyr Asp<br>-20 -15 -10 | | 1086 |
| TCC ACT GCC CGA ATC AGA AGG AAC GCC AAA GGA AAC TAC TGT AAG AGG<br>Ser Thr Ala Arg Ile Arg Arg Asn Ala Lys Gly Asn Tyr Cys Lys Arg<br>-5 1 5 | | 1134 |
| ACC CCG CTC TAC ATC GAC TTC AAG GAG ATT GGG TGG GAC TCC TGG ATC<br>Thr Pro Leu Tyr Ile Asp Phe Lys Glu Ile Gly Trp Asp Ser Trp Ile<br>10 15 20 25 | | 1182 |
| ATC GCT CCG CCT GGA TAC GAA GCC TAT GAA TGC CGT GGT GTT TGT AAC<br>Ile Ala Pro Pro Gly Tyr Glu Ala Tyr Glu Cys Arg Gly Val Cys Asn<br>30 35 40 | | 1230 |
| TAC CCC CTG GCA GAG CAT CTC ACA CCC ACA AAG CAT GCA ATT ATC CAG<br>Tyr Pro Leu Ala Glu His Leu Thr Pro Thr Lys His Ala Ile Ile Gln<br>45 50 55 | | 1278 |
| GCC TTG GTC CAC CTC AAG AAT TCC CAG AAA GCT TCC AAA GCC TGC TGT<br>Ala Leu Val His Leu Lys Asn Ser Gln Lys Ala Ser Lys Ala Cys Cys | | 1326 |

|  | 60 | | | | 65 | | | | 70 | | | | | | | |
|---|---|---|---|---|---|---|---|---|---|---|---|---|---|---|---|---|
| GTG | CCC | ACA | AAG | CTA | GAG | CCC | ATC | TCC | ATC | CTC | TAT | TTA | GAC | AAA | GGC | 1374 |
| Val | Pro | Thr | Lys | Leu | Glu | Pro | Ile | Ser | Ile | Leu | Tyr | Leu | Asp | Lys | Gly | |
| | 75 | | | | | 80 | | | | | 85 | | | | | |
| GTC | GTC | ACC | TAC | AAG | TTT | AAA | TAC | GAA | GGC | ATG | GCC | GTC | TCC | GAA | TGT | 1422 |
| Val | Val | Thr | Tyr | Lys | Phe | Lys | Tyr | Glu | Gly | Met | Ala | Val | Ser | Glu | Cys | |
| | 90 | | | | | 95 | | | | | 100 | | | | 105 | |
| GGC | TGT | AGA | TAGAAGAAGA | | GTCCTATGGC | | TTATTAATA | | ACTGTAAATG | | | | | | | 1471 |
| Gly | Cys | Arg | | | | | | | | | | | | | | |

TGTATATTTG GTGTTCCTAT TTAATGAGAT TATTTAATAA GGGTGTACAG TAATAGAGGC  1531

TTGCTGCCTT CAGGAAATGG ACAGGTCAGT TTGTTGTAGG AAATGCATAT TTT  1584

( 2 ) INFORMATION FOR SEQ ID NO:11:

( i ) SEQUENCE CHARACTERISTICS:
        ( A ) LENGTH: 424 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Gly  Ser  Leu  Val  Leu  Thr  Leu  Cys  Ala  Leu  Phe  Cys  Leu  Ala  Ala
-316 -315                -310                     -305

Tyr  Leu  Val  Ser  Gly  Ser  Pro  Ile  Met  Asn  Leu  Glu  Gln  Ser  Pro  Leu
-300                -295                     -290                          -285

Glu  Glu  Asp  Met  Ser  Leu  Phe  Gly  Asp  Val  Phe  Ser  Glu  Gln  Asp  Gly
               -280                     -275                          -270

Val  Asp  Phe  Asn  Thr  Leu  Leu  Gln  Ser  Met  Lys  Asp  Glu  Phe  Leu  Lys
               -265                     -260                          -255

Thr  Leu  Asn  Leu  Ser  Asp  Ile  Pro  Thr  Gln  Asp  Ser  Ala  Lys  Val  Asp
               -250                     -245                     -240

Pro  Pro  Glu  Tyr  Met  Leu  Glu  Leu  Tyr  Asn  Lys  Phe  Ala  Thr  Asp  Arg
          -235                     -230                     -225

Thr  Ser  Met  Pro  Ser  Ala  Asn  Ile  Ile  Arg  Ser  Phe  Lys  Asn  Glu  Asp
-220                -215                     -210                          -205

Leu  Phe  Ser  Gln  Pro  Val  Ser  Phe  Asn  Gly  Leu  Arg  Lys  Tyr  Pro  Leu
               -200                     -195                          -190

Leu  Phe  Asn  Val  Ser  Ile  Pro  His  His  Glu  Glu  Val  Ile  Met  Ala  Glu
                    -185                     -180                     -175

Leu  Arg  Leu  Tyr  Thr  Leu  Val  Gln  Arg  Asp  Arg  Met  Ile  Tyr  Asp  Gly
          -170                     -165                     -160

Val  Asp  Arg  Lys  Ile  Thr  Ile  Phe  Glu  Val  Leu  Glu  Ser  Lys  Gly  Asp
-155                     -150                     -145

Asn  Glu  Gly  Glu  Arg  Asn  Met  Leu  Val  Leu  Val  Ser  Gly  Glu  Ile  Tyr
-140                -135                     -130                          -125

Gly  Thr  Asn  Ser  Glu  Trp  Glu  Thr  Phe  Asp  Val  Thr  Asp  Ala  Ile  Arg
               -120                     -115                     -110

Arg  Trp  Gln  Lys  Ser  Gly  Ser  Ser  Thr  His  Gln  Leu  Glu  Val  His  Ile
               -105                     -100                          -95

Glu  Ser  Lys  His  Asp  Glu  Ala  Glu  Asp  Ala  Ser  Ser  Gly  Arg  Leu  Glu
          -90                      -85                      -80

Ile  Asp  Thr  Ser  Ala  Gln  Asn  Lys  His  Asn  Pro  Leu  Leu  Ile  Val  Phe
          -75                      -70                      -65

Ser  Asp  Asp  Gln  Ser  Ser  Asp  Lys  Glu  Arg  Lys  Glu  Glu  Leu  Asn  Glu
-60                 -55                      -50                           -45
```

| | | | | | | | | | | | | | | | |
|---|---|---|---|---|---|---|---|---|---|---|---|---|---|---|---|
| Met | Ile | Ser | His | Glu -40 | Gln | Leu | Pro | Glu | Leu -35 | Asp | Asn | Leu | Gly | Leu -30 | Asp |
| Ser | Phe | Ser | Ser -25 | Gly | Pro | Gly | Glu | Glu -20 | Ala | Leu | Leu | Gln | Met -15 | Arg | Ser |
| Asn | Ile | Ile -10 | Tyr | Asp | Ser | Thr | Ala -5 | Arg | Ile | Arg | Arg | Asn 1 | Ala | Lys | Gly |
| Asn 5 | Tyr | Cys | Lys | Arg | Thr 10 | Pro | Leu | Tyr | Ile | Asp 15 | Phe | Lys | Glu | Ile | Gly 20 |
| Trp | Asp | Ser | Trp | Ile 25 | Ile | Ala | Pro | Pro | Gly 30 | Tyr | Glu | Ala | Tyr | Glu 35 | Cys |
| Arg | Gly | Val | Cys 40 | Asn | Tyr | Pro | Leu | Ala 45 | Glu | His | Leu | Thr | Pro 50 | Thr | Lys |
| His | Ala | Ile 55 | Ile | Gln | Ala | Leu | Val 60 | His | Leu | Lys | Asn | Ser 65 | Gln | Lys | Ala |
| Ser | Lys 70 | Ala | Cys | Cys | Val | Pro 75 | Thr | Lys | Leu | Glu | Pro 80 | Ile | Ser | Ile | Leu |
| Tyr 85 | Leu | Asp | Lys | Gly | Val 90 | Val | Thr | Tyr | Lys | Phe 95 | Lys | Tyr | Glu | Gly | Met 100 |
| Ala | Val | Ser | Glu | Cys 105 | Gly | Cys | Arg | | | | | | | | |

( 2 ) INFORMATION FOR SEQ ID NO:12:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION:SEQ ID NO:12:

Arg Xaa Xaa Arg
1

DNA MOLECULES ENCODING BONE MORPHOGENETIC PROTEIN-10

This application is a continuation-in-part application of Ser. No. 08/061,695 filed on May 12, 1993 presently abandoned.

The present invention relates to a novel family of purified proteins designated Bone Morphogenetic Peptine-10 or BMP-10, DNA encoding them, and processes for obtaining them. These proteins may be used to induce bone and/or cartilage formation and in wound healing and tissue repair. These proteins may also be used for augmenting the activity of other bone morphogenetic proteins.

BACKGROUND OF THE INVENTION

The search for the molecule or molecules responsible for the bone and cartilage-inductive activity present in bone and other tissue extracts has led to the discovery of a novel set of molecules called the Bone Morphogenetic Proteins (BMPs). The structures of several proteins, designated BMP-1 through BMP-9, have previously been elucidated. The unique inductive activities of these proteins, along with their presence in bone, suggests that they are important regulators of bone repair processes, and may be involved in the normal maintenance of bone tissue. There is a need to identify whether additional proteins exist which play a role in these processes. The present invention relates to the identification of such a protein, which the inventors have designated BMP-10.

SUMMARY OF THE INVENTION

Bovine BMP-10

The bovine BMP-10 DNA sequence (SEQ ID NO: 1) and amino acid sequence (SEQ ID NO: 2) are set forth in the Sequence Listings. BMP-10 proteins are capable of inducing the formation of cartilage, bone or combinations thereof. BMP-10 proteins may be further characterized by the ability to demonstrate cartilage and/or bone formation activity in the rat bone formation assay described below.

Bovine BMP-10 may be produced by culturing a cell transformed with a DNA sequence comprising nucleotide a DNA sequence encoding the mature BMP-10 polypeptide, comprising nucleotide #779 to nucleotide #1102 as shown in SEQ ID NO: 1, and recovering and purifying from the culture medium a protein characterized by the amino acid sequence comprising amino acids #1 to #108 as shown in SEQ ID NO:2 substantially free from other proteinaceous materials with which it is co-produced. For production in mammalian cells, the DNA sequence further comprises a DNA sequence encoding a suitable propeptide 5' to and linked in frame to the nucleotide sequence encoding the mature BMP-10 polypeptide. The propeptide may be the native BMP-10 propeptide, or may be a propeptide from another protein of the TGF-β superfamily.

Human BMP-10 is expected to be homologous to bovine BMP-10. The invention, therefore, includes methods for obtaining the DNA sequences encoding human BMP-10, the DNA sequences obtained by those methods, and the human protein encoded by those DNA sequences. This method entails utilizing the bovine BMP-10 nucleotide sequence or portions thereof to design probes to screen libraries for the human gene or coding sequences or fragments thereof using standard techniques. A DNA sequence encoding part of the human BMP-10 protein (SEQ ID NO:3) and the corresponding amino acid sequence (SEQ ID NO:4) are set forth herein. These sequences may also be used in order to design probes to obtain the complete human BMP-10 gene or coding sequences through standard techniques. Human BMP-10 may be produced by culturing a cell transformed with the BMP-10 DNA sequence and recovering and purifying BMP-10 from the culture medium. The purified expressed protein is substantially free from other proteinaceous materials with which it is co-produced, as well as from other contaminants. The recovered purified protein is contemplated to exhibit cartilage and/or bone formation activity. The proteins of the invention may be further characterized by the ability to demonstrate cartilage and/or bone formation activity in the rat bone formation assay described below.

Another aspect of the invention provides pharmaceutical compositions containing a therapeutically effective amount of a BMP-10 protein in a pharmaceutically acceptable vehicle or carrier. BMP-10 compositions of the invention may be used in the formation of cartilage. These compositions may further be utilized for the formation of bone. BMP-10 compositions may also be used for wound healing and tissue repair. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432.

The compositions of the invention may comprise, in addition to a BMP-10 protein, other therapeutically useful agents including growth factors such as epidermal growth factor (EGF), fibroblast growth factor (FGF), transforming growth factor (TGF-α and TGF-β), and insulin-like growth factor (IGF). The compositions may also include an appropriate matrix for instance, for supporting the composition and providing a surface for bone and/or cartilage growth. The matrix may provide slow release of the osteoinductive protein and/or the appropriate environment for presentation thereof.

The BMP-10 compositions may be employed in methods for treating a number of bone and/or cartilage defects, periodontal disease and various types of wounds. These methods, according to the invention, entail administering to a patient needing such bone and/or cartilage formation wound healing or tissue repair, an effective amount of a BMP-10 protein. These methods may also entail the administration of a protein of the invention in conjunction with at least one of the novel BMP proteins disclosed in the co-owned applications described above. In addition, these methods may also include the administration of a BMP-10 protein with other growth factors including EGF, FGF, TGF-α, TGF-β, and IGF.

Still a further aspect of the invention are DNA sequences coding for expression of a BMP-10 protein. Such sequences include the sequence of nucleotides in a 5' to 3' direction illustrated in SEQ ID NO: 1 or SEQ ID NO: 10, DNA sequences which, but for the degeneracy of the genetic code, are identical to the DNA sequence SEQ ID NO: 1 or SEQ ID NO: 10, and encode the protein of SEQ ID NO: 2 or SEQ ID NO: 11. Further included in the present invention are DNA sequences which hybridize under stringent conditions with the DNA sequence of SEQ ID NO: 1 or SEQ ID NO: 10 and encode a protein having the ability to induce the formation of cartilage and/or bone. Preferred DNA sequences include those which hybridize under stringent conditions [see, T. Maniatis et al, *Molecular Cloning (A Laboratory Manual)*, Cold Spring Harbor Laboratory (1982), pages 387 to 389]. Finally, allelic or other variations of the sequences of SEQ ID NO: 1 or SEQ ID NO: 10, whether such nucleotide changes result in changes in the peptide sequence or not, but where the peptide sequence still has BMP-10 activity, are also included in the present invention.

A further aspect of the invention includes vectors comprising a DNA sequence as described above in operative association with an expression control sequence therefor. These vectors may be employed in a novel process for producing a BMP-10 protein of the invention in which a cell line transformed with a DNA sequence encoding a BMP-10 protein in operative association with an expression control sequence therefor, is cultured in a suitable culture medium and a BMP-10 protein is recovered and purified therefrom. This process may employ a number of known cells both prokaryotic and eukaryotic as host cells for expression of the polypeptide.

The vectors may be used in gene therapy applications. In such use, the vectors may be transfected into the cells of a patient in vitro, and the cells may be reintroduced into a patient. Alternatively, the vectors may be introduced into a patient in vivo through targeted transfection.

Descripton of the Sequences

SEQ ID NO:1 is the nucleotide sequence encoding part of the bovine BMP-10, derived from clone λ7r-20.

SEQ ID NO:2 is the amino acid sequence containing the mature bovine BMP-10 polypeptide.

SEQ ID NO:3 is a partial nucleotide sequence of human BMP-10.

SEQ ID NO:4 is a partial amino acid sequence for human BMP-10 polypeptide.

SEQ ID NO:5 and 6 are primers to bovine BMP-10 used to isolate the human BMP-10 or other BMP-10 proteins.

SEQ ID NO:7 is a DNA sequence that is inserted into pMT2 CXM to add an XhoI recognition site near the SV40 origin of replication.

SEQ ID NO:8 is a DNA sequence inserted into pMT21 to insert an XhoI recognition site upstream from the DHFR gene.

SEQ ID NO:9 is a DNA sequence comprising a portion of the EMC virus leader sequence.

SEQ ID NO: 10 is a DNA sequence encoding the complete human BMP-10 protein, including the complete propeptide at nucleotides #160 to #1107, and the mature polypeptide at nucleotides #1108 to #1431, derived from the cDNA clone HFL-3 and the genomic clone 20GEN.3.

SEQ ID NO: 11 is the amino acid sequence encoded by SEQ ID NO:10.

SEQ ID NO: 12 is the consensus amino acid sequence of the consensus proteolytic processing site.

DETAILED DESCRIPTION OF THE INVENTION

BMP-10

The bovine BMP-10 nucleotide sequence (SEQ ID NO: 1) and encoded amino acid sequence (SEQ ID NO: 2) are set forth in the Sequence listings herein. The coding sequence of the mature bovine BMP-10 protein begins at nucleotide #779 and continues through nucleotide #1102. Purified bovine BMP-10 proteins of the present invention are produced by culturing a host cell transformed wth a DNA sequence comprising the DNA coding sequence of SEQ ID NO: 1 from nucleotide #167 to #1102, or from nucleotide #779 to #1102, and recovering and purifying from the culture medium a protein which contains the amino acid sequence or a substantially homologous sequence as represented by amino acids #-204 to #108 or #1 to #108 of SEQ ID NO: 2. A host cell may be transformed with a coding sequence encoding a propeptide suitable for the secretion of proteins by the host cell is linked in proper reading frame to the coding sequence for the mature BMP-10 protein. For example, see U.S. Pat. No. 5,168,050, the disclosure of which is hereby incorporated by reference, in which a DNA encoding a precursor portion of a mammalian protein other than BMP-2 is fused to the DNA encoding a mature BMP-2 protein. Thus, the present invention includes chimeric DNA molecules comprising a DNA sequence encoding a propeptide from a member of the TGF-β superfamily of proteins, other than BMP-10, is linked in correct reading frame to a DNA sequence encoding a BMP-10 polypeptide. The term "chimeric" is used to signify that the propeptide originates from a different polypeptide than the BMP-10.

The human BMP-10 sequence of the present invention is obtained using the whole or fragments of the bovine BMP-10 DNA sequence, or the partial human BMP-10 sequence of SEQ ID NO:3, as a probe. Thus, the human BMP-10 DNA sequence comprise the DNA sequence of nucleotides #30 to #167 of SEQ ID NO: 3. This partial sequence of the human BMP-10 DNA sequence corresponds well to nucleotides #899 to #1036 of the bovine BMP-10 DNA sequence shown in SEQ ID NO: 1. The human BMP-10 protein comprises the sequence of amino acids #1–#46 of SEQ ID NO: 4. It is expected that BMP-10, as expressed by mammalian cells such as CHO cells, exists as a heterogeneous population of active species of BMP-10 protein with varying N-termini. It is expected that active species will comprise an amino acid sequence beginning with the cysteine residue at amino acid #7 of SEQ ID NO:1, or will comprise additional amino acid sequence further in the N-terminal direction. Thus, it is expected that DNA sequences encoding active BMP-10 proteins will comprise a nucleotide sequence comprising nucleotides #779 or #797 to #1102 of SEQ ID NO:1 or nucleotides #1108 or #1126 to #1431 of SEQ ID NO:10.

The N-terminus of human BMP-10 has been experimentally determined by expression in $E.\ coli$ to be as follows: [M]NAKGNYXKRTPLYIDFKEI, consistent with amino acids 1 to 19 of SEQ ID NO:11 wherein X designates an amino acid residue with no clear signal, which is consistent with a cysteine residue at that location. Thus, it appears that the N-terminus of this species of BMP-10 is at amino acid #1 of SEQ ID NO:1 or SEQ ID NO:10, and a DNA sequence encoding said species of BMP-10 would comprise nucleotides #779 to 1102 of SEQ ID NO:1 or #1108 to 1431 of SEQ ID NO:10. The apparent molecular weight of human Activin WC monomer was determined by SDS-PAGE to be approximately 10–12 kd on a Novex 16% tricine gel. Molecular weight of monomer by electrospray ionization mass spectrometry is 12292.5 on a Finnigan TSQ 7000. The human BMP-10 protein exists as a clear, colorless solution in 0.1% trifluoroacetic acid.

The BMP-10 proteins recovered from the culture medium are purified by isolating them from other proteinaceous materials from which they are co-produced and from other contaminants present. BMP-10 proteins may be characterized by the ability to induce the formation of cartilage and/or bone, for example, in the rat bone formation assay described below.

The BMP-10 proteins provided herein also include factors encoded by the sequences similar to those of SEQ ID NO: 1, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO: 2. These sequences, by virtue of sharing primary, secondary, or tertiary structural and conformational characteristics with bone growth factor polypeptides of SEQ ID NO: 2 may possess bone growth factor biological properties in common therewith. Thus, they may be employed as biologically active substitutes for naturally-occurring BMP-10 and other BMP-10 polypeptides in therapeutic processes.

Other specific mutations of the sequences of BMP-10 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of BMP-10 protein will also result in production of a non-glycosylated protein, even if the glycosylation sites are left unmodified.

The present invention also encompasses the novel DNA sequences, free of association with DNA sequences encoding other proteinaceous materials, and coding for expression of BMP-10 proteins. These DNA sequences include those depicted in SEQ ID NO: 1 in a 5' to 3' direction and those sequences which hybridize thereto under stringent hybridization conditions [for example, 0.1× SSC, 0.1% SDS at 65° C.; see, T. Maniatis et al, *Molecular Cloning (A Laboratory Manual)*, Cold Spring Harbor Laboratory (1982), pages 387 to 389] and encode a protein having cartilage and/or bone inducing activity. These DNA sequences also include those which comprise the DNA sequence of SEQ ID NO: 3 and those which hybridize thereto under stringent hybridization conditions and encode a protein having cartilage and/or bone inducing activity.

Similarly, DNA sequences which code for BMP-10 proteins coded for by the sequences of SEQ ID NO: 1, or BMP-10 proteins which comprise the amino acid sequence of SEQ ID NO: 2, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 3 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-10 proteins. The method of the present invention involves culturing a suitable cell line, which has been transformed with a DNA sequence encoding a BMP-10 protein of the invention, under the control of known regulatory sequences. The transformed host cells are cultured and the BMP-10 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of BMP-10 may not be necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-10 polypeptides. Preferably the vectors contain the full novel DNA sequences described above which encode the novel factors of the invention. Additionally, the vectors contain appropriate expression control sequences permitting expression of the BMP-10 protein sequences. Alternatively, vectors incorporating modified sequences as described above are also embodiments of the present invention. Additionally, the sequence of SEQ ID NO:1 or other sequences encoding BMP-10 proteins could be manipulated to express a mature BMP-10 protein by deleting BMP-10 encoding propeptide sequences and replacing them with sequences encoding the complete propeptides of other BMP proteins or members of the TGF-β superfamily. Thus, the present invention includes chimeric DNA molecules encoding a propeptide from a member of the TGF-β superfamily linked in correct reading frame to a DNA sequence encoding a BMP-10 polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces cartilage and/or bone formation in circumstances where bone is not normally formed, has application in the healing of bone fractures and cartilage defects in humans and other animals. Such a preparation employing a BMP-10 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-10 protein may be used in the treatment of periodontal disease, and in other tooth repair processes. Such agents may provide an environment to attract bone-forming cells, stimulate growth of bone-forming cells or induce differentiation of progenitors of bone-forming cells. BMP-10 polypeptides of the invention may also be useful in the treatment of osteoporosis. A variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to cartilage and/or bone defects or periodontal diseases. The invention further comprises therapeutic methods and compositions for wound healing and tissue repair. Such compositions comprise a therapeutically effective amount of at least one of the BMP-10 proteins of the invention in admixture with a pharmaceutically acceptable vehicle, carrier or matrix.

It is expected that the proteins of the invention may act in concert with or perhaps synergistically with other related proteins and growth factors. Further therapeutic methods and compositions of the invention therefore comprise a therapeutic amount of at least one BMP-10 protein of the invention with a therapeutic amount of at least one of the other BMP proteins disclosed in co-owned applications described above. Such combinations may comprise separate molecules of the BMP proteins or heteromolecules comprised of different BMP moieties. For example, a method and composition of the invention may comprise a disulfide linked dimer comprising a BMP-10 protein subunit and a subunit from one of the "BMP" proteins described above. Thus, the present invention includes a purified BMP-10 polypeptide which is a heterodimer wherein one subunit comprises at least the amino acid sequence from amino acid #1 to amino acid #108 of SEQ ID NO:2, and one subunit comprises an amino acid sequence for a bone morphogenetic protein selected from the group consisting of BMP-1, BMP-2, BMP-3, BMP-4, BMP-5, BMP-6, BMP-7, BMP-8 and BMP-9. A further embodiment may comprise a heterodimer of BMP-10 moieties. Further, BMP-10 proteins may be combined with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), and k-fibroblast growth factor (kFGF), parathyroid hormone (PTH), leukemia inhibitory factor (LIF/HILDA/DIA), insulin-like growth factors (IGF-I and IGF-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with the BMP-10 proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-10 proteins which may also optionally be included in the composition as described above, may alternatively or additionally, be administered simultaneously or sequentially with the BMP composition in the methods of the invention.

Preferably for bone and/or cartilage formation, the composition includes a matrix capable of delivering BMP-10 or other BMP proteins to the site of bone and/or cartilage damage, providing a structure for the developing bone and cartilage and optimally capable of being resorbed into the body. The matrix may provide slow release of BMP-10 and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the BMP-10 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-10 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage.

Progress can be monitored by periodic assessment of bone growth and/or repair. The progress can be monitored, for example, x-rays, histomorphometric determinations and tetracycline labeling.

The following examples illustrate practice of the present invention in recovering and characterizing bovine BMP-10 protein and employing it to recover the human and other BMP-10 proteins, obtaining the human proteins and expressing the proteins via recombinant techniques.

EXAMPLE 1

Bovine BMP-10

800,000 recombinants of a bovine genomic library constructed in the vector λEMBL3 are plated at a density of 8000 recombinant bacteriophage plaques per plate on 100 plates. Duplicate nitrocellulose replicas of the recombinant bacteriophage plaques are made from these plates and amplified. A fragment of human BMP-7 DNA corresponding to nucleotides #1081 to #1403 (FIG. 4, U.S. Pat. No. 5,141,905) is $^{32}$P-labelled by the random priming procedure of Feinberg et al. [Anal. Biochem. 132: 6–13 (1983)] and hybridized to one set of filters in standard hybidization buffer (5× SSC, 0.1% SDS, 5× Denhardt's, 100 μg/ml salmon sperm DNA)(SHB) at 60° C. for 2 to 3 days. The filters are washed under reduced stringency conditions (4× SSC, 0.1% SDS at 60° C.). Multiple positively hybridizing recombinants are noted. 52 positively hybridizing recombinant bacteriophage plaques are selected and replated for secondaries. Duplicate nitrocellulose replicas of the recombinant plaques are made from these 52 secondary plates and amplified.

One set of nitrocellulose filters is hybridized to the human BMP-7 DNA probe as described above and washed under the same reduced stringency conditions. The other set of filters is hybridized to a mixed BMP-5, BMP-6, and BMP-7 probe in SHB at 65° C. overnight and washed with a 0.1× SSC, 0.1% SDS at 65° C. (stringent hybridization and wash conditions). The mixed probe consists of relatively equal amounts of $^{32}$P-labelled DNA fragments comprising nucleotides #1452 to #2060 (FIG. 4, U.S. Pat. No. 5,106,748) of the human BMP-5 sequence, nucleotides #1395 to #1698 (FIG. 4, U.S. Pat. No. 5,187,076) of the human BMP-6 sequence, and nucleotides #1081 to #1403 (FIG. 4, U.S. Pat. No. 5,141,905) of the human BMP-7 sequence. The BMP-5, BMP-6 and BMP-7 DNA fragments are $^{32}$P-labelled by the random priming procedure and equal numbers of counts per minute (cpms) of each probe are combined and added to the SHB containing the other set of nitrocellulose filter replicas of the 52 secondary plates.

Fourteen recombinants, which hybridized positively to the human BMP-7 probe under the reduced stringency conditions and exhibited weak or no hybridization to the mixed BMP-5/6/7 probe under high stringency conditions, are selected for further analysis. All 14 recombinants which exhibit these hybridization characteristics are plaque purified and bacteriophage DNA is prepared from each. The positively hybridizing region of one of the recombinants, designated λ7r-20, is localized to a 0.5 kb EcoRI/HindIII restriction fragment. This fragment is subcloned into a plasmid vector (pGEM-3) and DNA sequence analysis is performed. The partial DNA sequence (SEQ ID NO: 1) and derived amino acid sequence (SEQ ID NO: 2) of clone λ7r-20 are shown in the Sequence Listings.

The bacteriophage λ7r-20 has been deposited with the American Type Culture Collection, 12301 Parklawn Drive, Rockville, Md., 20852, on Apr. 23, 1993 and has been given the accession number ATCC 75452. This deposit meets the requirements of the Budapest Treaty of the International Recognition of the Deposit of Microorganisms for the Purpose of Patent Procedures and regulations thereunder.

This λ7r-20 clone encodes at least a portion of the bovine BMP-10 protein of the present invention. The nucleotide sequence of clone λ7r-20 contains an open reading frame of at least 938 bp, as defined by nucleotides #165 to #1102 of SEQ ID NO:1 (#165–166 being the last two thirds of a codon which is interrupted by an intron). The open reading frame encodes at least 312 amino acids of a BMP-10 protein. The encoded 312 amino acid BMP-10 protein includes the full mature bovine BMP-10 protein (amino acid #1 to #108 of SEQ ID NO:2), as well as the C-terminal portion of the propeptide region of the primary translation product (amino acid #-204 to #-1 of SEQ ID NO:2). A consensus splice acceptor sequence immediately preceding the BMP-10 coding sequence at #165 to #1102, and an in frame stop codon at position #101 to #103, suggests the presence of intron sequences in the 5' direction of nucleotide #165.

Based upon the knowledge of other BMP proteins and other proteins within the TGF-β family, it is predicted that the precursor polypeptide would be cleaved at the multibasic sequence ARG-ILE-ARG-ARG consistent with amino acids −4 to −1 of SEQ ID NO:11 in agreement with a proposed consensus proteolytic processing sequence of ARG-X-X-ARG (SEQ ID NO:12). Cleavage of the BMP-10 precursor polypeptide is expected to generate a 108 amino acid mature peptide beginning with the amino acid ASN at position #1. The processing of BMP-10 into the mature form is expected to involve dimerization and removal of the N-terminal region in a manner analogous to the processing of the related protein TGF-β [Gentry et al., *Molec. & Cell. Biol.,* 8:4162 (1988); Derynck et al., *Nature,* 316:701(1985)].

It is contemplated therefore that the mature active species of BMP-10 comprises a homodimer of two polypeptide subunits, each subunit comprising amino acids #1 to #108 with a predicted molecular weight of approximately 12,000 daltons. Further active species are contemplated comprising amino acids #7 to #108, thereby including the first conserved cysteine residue. As with other members of the BMP and TGF-β family of proteins, the carboxy-terminal region of the BMP-10 protein exhibits greater sequence conservation than the more amino-terminal portion. The percent amino acid identity of the bovine BMP-10 protein in the cysteine-rich C-terminal domain (amino acids #7 to #108) to the corresponding region of other human BMP proteins and other proteins within the TGF-β family is as follows: BMP-2, 56%; BMP-3, 39%; BMP-4, 54%; BMP-5, 48%, BMP-6, 48%; BMP-7, 47%; BMP-8, 46%; BMP-9, 67%' Vg1, 50%; GDF-1, 40%; TGF-β1, 37%; TGF-β2, 37%; TGF-β3, 37%; inhibin β(B), 36%; inhibin β(A), 39%.

EXAMPLE 2

Human BMP-10

Bovine and human osteoinductive factor genes are presumed to be significantly homologous, therefore the bovine coding sequence or a portion thereof is used as a probe to screen a human genomic library or as a probe to identify a human cell line or tissue which synthesizes the analogous human cartilage and/or bone protein. A human genomic library, such as Stratagene catalog #944201, may be screened with such a probe, and presumptive positives isolated and DNA sequence obtained. Evidence that this recombinant encodes a portion of the human BMP-10 relies of the bovine/human protein and gene structure homologies.

Once a recombinant bacteriophage containing DNA encoding a portion of the human cartilage and/or bone inductive factor molecule is obtained, the human coding sequence can be used as a probe to identify a human cell line or tissue which synthesizes BMP-10 mRNA. Alternatively, the bovine BMP-10 coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the bovine or human BMP-10. Alternatively, the bovine BMP-10 coding sequence is used to design oligonucleotide primers which will specifically amplify a portion of the BMP-10 encoding sequence located in the region located between the primers utilized to perform the specific amplification reaction. It is contemplated that bovine and human BMP-10 sequences would allow one to specifically amplify corresponding human BMP-10 encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other λ bacteriophage vectors known to those skilled in the art, for example, λ ZAP by established techniques (Toole et al., supra). It is also possible to perform the oligonucleotide primer directed amplification reaction, described above, directly on a pre-established human cDNA or genomic library which has been cloned into a λ bacteriophage vector. In such cases, a library which yields a specifically amplified DNA product encoding a portion of human BMP-10 protein could be screened directly, utilizing the fragment of amplified BMP-10 encoding DNA as a probe.

Oligonucleotide primers designed on the basis of the DNA sequence of the bovine BMP10 genomic clone λ7r-20 are predicted to allow the specific amplification of human BMP-10 encoding sequences. The following oligonucleotide primer is designed on the basis of nucleotides #876 to #898 of the DNA sequence set forth in SEQ ID NO. 1 and synthesized on an automated DNA synthesizer.

Primer A:
TGCTCTAGACCTATGAATGTCGTGGTGTTTGC
(SEQ ID NO:5)

The first nine nucleotides of primer A (underlined) comprise the recognition sequence for the restriction endonuclease XbaI which can be utilized to facilitate the manipulation of a specifically amplified DNA sequence encoding the BMP-10 protein of the invention and are thus not derived from the DNA sequence presented in SEQ ID NO: 1.

The following oligonucleotide primer is designed on the basis of nucleotides #1060 to #1037 of the DNA sequence set forth in SEQ ID NO. 1 and synthesized on an automated DNA synthesizer:

Primer B:
TAGGGATCCCTTGTAGGTGACGACGCCCTTATC
(SEQ ID NO:6)

The first nine nucleotides of primer B (underlined) comprise the recognition sequence for the restriction endonuclease BamHI which can be utilized to facilitate the manipulation of a specifically amplified DNA sequence encoding the BMP-10 protein of the invention and are thus not derived from the DNA sequence present in SEQ ID NO: 1.

The standard nucleotide symbols in the above identified primers are as follows: A, adenosine; C, cytosine, G, guanine; and T, thymine.

Primers A and B identified above are utilized as primers to allow the amplification of a specific nucleotide from human genomic DNA. the amplification reaction is performed as follows:

Human genomic DNA (source: peripheral blood lymphocytes) is denatured at 100° C. for five minutes and then chilled on ice prior to addition to a reaction mixture containing 200 μM each deoxynucleotide triphosphates (dATP, dGTP, dCTP and dTTP) 10 mM Tris-HCl pH8.3, 50mM KCl, 1.5mM MgCl$_2$, 0.001% gelatin, 1.25 units Taq DNA polymerase, 100 pM oligonucleotide primer A and 100 pM oligonucleotide primer B. This reaction mixture is then subjected to thermal cycling in the following manner: 3 minutes at 94° C., 1 minute at 50° C., 1 minute at 72° C. for one cycle, then 1 minute at 94° C., 1 minute at 50° C., 1 minute at 72° C. for thirty-nine cycles.

The DNA which is specifically amplified by this reaction is separated from the excess oligonucleotide primers A and B utilized to initiate the amplification by the use of a DNA purification resin based protocol under the conditions suggested by the manufacturer. The resulting DNA product is digested with the restriction endonucleases XbaI and BamHI, phenol extracted, chloroform extracted. Buffer exchange and removal of small fragments of DNA resulting from the XbaI/BaHI restriction digest is accomplished by dilution of the digested DNA product in 10 mM Tris-HCl pH8.0, 1 mM EDTA followed by centrifugation through a centricon™ 30 microconcentrator (W.R. Grace & Co., Beverly, Mass.; Product #4209). The resulting XbaI/BamHI digested amplified DNA product is subcloned into a plasmid vector (pBluescript) between the XbaI and BamHI restriction sites of the polylinker region. DNA sequence analysis of the resulting subclones indicates that the specifically amplified DNA sequence product encodes a portion of the human BMP-10 protein of this invention. The DNA sequence (SEQ ID NO. 3) and derived amino acid sequence (SEQ ID NO. 4) of this specifically amplified DNA fragment are set forth in the Sequence Listings.

Nucleotides #1 to #29 of this sequence comprise a portion of oligonucleotide primer A and nucleotides #168 to #197 comprise a portion of oligonucleotide primer B utilized to perform the specific amplification reaction. Due to the function of oligonucleotide primers A and B (designed on the basis of bovine BMP-10 DNA sequence) in initiating the amplification reaction, they may not correspond exactly to the actual sequence encoding a human BMP-10 and are therefore not translated in the above amino acid sequence derivation. The DNA sequence, from nucleotide #30 to #167 of SEQ ID NO: 3, or portions thereof, specifically amplified from the human genomic DNA template can be utilized as a probe to identify additional human BMP-10 encoding sequences from human genomic or human cDNA libraries by standard hybridization/screening techniques known to those skilled in the art.

Full-length Human BMP-10

The full-length human BMP-10 DNA sequence (SEQ ID NO:10) and encoded amino acids sequence (SEQ ID NO:11) are described in the Sequence Listings.

One million recombinants of a human fetal liver cDNA library (Clonetech catalog #HL 1064a) constructed in the vector λgt10 are plated at a density of 20,000 recombinant bacteriophge plaques per plate on 50 plates. Duplicate nitrocellulose replicas of the recombinant bacteriophage plaques are made from these plates. An oligonucleotide probe designed on the basis of nucleotides #85–#114 of SEQ ID NO:3 is synthesized on an automated DNA synthesizer. This oligonucleotide probe is radioactively labelled with $\gamma^{32}$P-ATP and is hybridized to both sets of the duplicate nitrocellulose replicas in SHB at 65° C. Eleven positively hybridizing recombinants are noted. One of the positively hybridizing recombinants, named HFL-3, is plaque purified. Bacteriophage plate stocks of the purified HFL-3 cDNA clone are prepared and bacteriophage DNA is isolated. A bacteriophage stock of this cDNA clone has been deposited with the ATCC, 12301 Parklawn Drive, Rockville, Md. USA under the requirements of the Budapest Treaty and designated as ATCC #75776. A portion of the DNA sequence of clone HFL-3 is set forth in SEQ ID NO: 10.

One million recombinants of a human genomic library (Stratagene Catalog #944201) constructed in the vector λFIX are plated at a density of 20,000 recombinant bacteriophge plaques per plate on 50 plates. Duplicate nitrocellulose replicas of the recombinant bacteriophage plaques are made from these plates. An oligonucleotide probe designed on the basis of nucleotides #355–+190384 of SEQ ID NO:10 is synthesized on an automated DNA synthesizer. This oligonucleotide probe is radioactively labelled with $\gamma^{32}P$-ATP and is hybridized to both sets of the duplicate nitrocellulose replicas in SHB at 65° C. Six positively hybridizing recombinants are noted. One of the positively hybridizing recombinants, named 20GEN.3, is plaque purified. Bacteriophage plate stocks of the purified 20GEN.3 genomic clone are prepared and bacteriophage DNA is isolated. A bacteriophage stock of this genomic clone has been deposited with the ATCC, 12301 Parklawn Drive, Rockville, Md. USA under the requirements of the Budapest Treaty and designated as ATCC #75774. A portion of the DNA sequence of clone 20GEN.3 is set forth in SEQ ID NO: 10. A portion of the DNA sequence of the genomic clone 20GEN.3 was determined to be identical to a portion of the DNA sequence of the cDNA clone HFL-3. The extent of this overlap (nucleotides #219–#316) of SEQ ID NO:10 were used as a basis to compile the complete coding sequence of the BMP-10 protein. This sequence is presented in SEQ ID NO:10 and it should be noted that nucleotides #1–#218 are derived entirely from the DNA sequence contained in genomic clone 20GEN.3 and nucleotides #317–#1584 are derived entirely from the DNA sequence contained in cDNA clone HFL-3, while nucleotides #219– #316 have been determined to be present in both 20GEN.3 and HFL-3. SEQ ID NO:10 predicts a human BMP10 precursor protein of 424 amino acids. Based on the knowledge of other BMPs and other proteins within the TGF-β family, it is predicted that the precursor polypeptide would be cleaved at the multibasic sequence ARG-ILE-ARG-ARG (amino acids #-4 through #-1 of SEQ ID NO:11) in agreement with the proposed consensus proteolytic processing sequence ARG-X-X-ARG. Cleavage of the human BMP-10 precursor polypeptide at this location would generate a 108 amino acid mature peptide beginning with the amino acid ASN at position #1 of SEQ ID NO:11. The processing of human BMP-10 into the mature form is expected to involve dimerization and removal of the N-terminal region in a manner analogous to the processing of the related protein TGF-β [L. E. Gentry, et al. Molec. & Cell. Biol. 8:4162 (1988); R. Derynck, et al., Nature 316:701 (1985). It is contemplated that the mature active species of human BMP-10 comprises a homodimer of two polypeptide subunits, each subunit comprising amino acids #1–#108 of SEQ ID NO:11, with a predicted molecular weight of 12,000 daltons. Further active species are contemplated comprising amino acids #7–#108 thereby including the first conserved cysteine residue. Heterodimeric molecules comprising one subunit of BMP-10 and another subunit of another member of the BMP/TGF-β superfamily are also contemplated.

Additional methods known to those skilled in the art may be used to isolate other species BMP-10 proteins of the invention.

EXAMPLE 3

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 Units/ml penicillin+100 μg/ml streptomycin. The cells are allowed to attach overnight in a 95% air, 5% $CO_2$ incubator at 37° C.

The 200 μl of media is removed from each well with a multichannel pipettor and replaced with an equal volume of test sample delivered in DME with 10% heat inactivated fetal calf serum, 2mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 μl per well of calcium/magnesium free phosphate buffered saline and these washes are discarded.

50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 μl of 0.2N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

| Absorbance Values for Known Standards of P-Nitrophenol Phosphate | |
|---|---|
| P-nitrophenol phosphate umoles | Mean absorbance (405 nm) |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to μmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-10 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE 4

ROSEN MODIFIED SAMPATH-REDDI ASSAY

A modified version of the rat bone formation assay described in Sampath and Reddi, *Proc. Natl. Acad. Sci. USA*, 80:6591–6595 (1983) is used to evaluate bone and/or cartilage activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

The BMP-10 proteins of this invention may be assessed for activity on this assay.

EXAMPLE 5

Expression of BMP-10

In order to produce bovine, human or other mammalian BMP-10 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-10 is contemplated to be stably transformed mammalian cells.

One skilled in the art can construct mammalian expression vectors by employing the sequence of SEQ ID NO: 1 or SEQ ID NO: 10, or other DNA sequences encoding BMP-10 proteins or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga, et al., Biotechnology 84: 636 (1984). This removes bases 1075 to 1145 relative to the Hind III site near the SV40 origin of replication and enhancer sequences of pMT2. In addition it inserts the following sequence:

5'PO-CATGGGCAGCTCGAG-3' (SEQ ID NO:7)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'

5'-CGAGGTTAAAAAACGTCTAGGCCCCCCGAACCACGGGGACGTGGTTTTCCTTTGAAAAACACGATTGC-3' (SEQ ID NO:8)
TaqI

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-10 DNA sequences. For instance, BMP-10 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-10 proteins. Additionally, the sequence of SEQ ID NO:1 or SEQ ID NO: 10 or other sequences encoding BMP-10 proteins can be manipulated to express a mature BMP-10 protein by deleting BMP-10 encoding propeptide sequences and replacing them with sequences encoding the complete propeptides of other BMP proteins.

One skilled in the art can manipulate the sequences of SEQ ID NO: 1 or SEQ ID NO: 10 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-10 coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a BMP-10 protein expressed thereby. For a strategy for producing extracellular expression of BMP-10 proteins in bacterial cells, see, e.g. European patent application EPA 177, 343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

5'—CGAGGTTAAAAAACGTCTAGGCCCCCCGAACCACGGGGACGTGGTTTTCCTTTGAAAAACACGATTGC—3' (SEQ ID NO:9)
TaqI                                                                            XhoI

A method for producing high levels of a BMP-10 protein of the invention in mammalian cells may involve the construction of cells containing multiple copies of the heterologous BMP-10 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a BMP-10 of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electropotation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5:1750 (1983). Transformants are cloned, and biologically active BMP-10 expression is monitored by the Rosen-modified Sampath-Reddi rat bone formation assay described above in Example 4. BMP-10 expression should increase with increasing levels of MTX resistance. BMP-10 polypeptides are characterized using standard techniques known in the art such as pulse labeling with [35S] methionine or cysteine and polyacrylamide gel electrophoresis. Similar procedures can be followed to produce other related BMP-10 proteins.

EXAMPLE 6

Biological Activity of Expressed BMP-10

To measure the biological activity of the expressed BMP-10 proteins obtained in Example 5 above, the proteins are recovered from the cell culture and purified by isolating the BMP-10 proteins from other proteinaceous materials with which they are co-produced as well as from other contaminants. The purified protein may be assayed in accordance with the rat bone formation assay described in Example 4.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA molecule comprising a DNA sequence selected from the group consisting of:
   (a) nucleotide #779 or 797 to #1102 of SEQ ID NO:1;
   (b) nucleotides #1108 or 1126 to #1431 of SEQ ID NO:10;
   (c) nucleotides encoding amino acids 1 or 7 to 108 of SEQ ID NO:2;
   (d) nucleotides encoding amino acids 1 or 7 to 108 of SEQ ID NO:11; and
   (e) naturally occurring allelic sequences and equivalent degenerative codon sequences of (a) or (b).

2. A host cell transformed with a DNA molecule of claim 1.

3. A vector comprising a DNA molecule of claim 1 in operative association with an expression control sequence therefor.

4. A host cell transformed with the vector of claim 3.

5. An isolated DNA molecule comprising a DNA sequence selected from the group consisting of nucleotides #779 to #1102 of SEQ ID NO:1 and nucleotides #1108 to #1431 of SEQ ID NO:10.

6. A vector comprising a DNA molecule of claim 5 in operative association with an expression control sequence therefor.

7. A host cell transformed with the vector of claim 6.

8. A method for producing a purified bone morphogenetic protein-10 (BMP-10) protein, said method comprising the steps of:
   (a) culturing a host cell transformed with a DNA molecule according to claim 1; and
   (b) recovering and purifying said BMP-10 protein from the culture medium.

9. The method of claim 8, wherein said host cell is transformed with a DNA molecule comprising a DNA coding sequence selected from the group consisting of:
   (a) nucleotide #779 to #1102 of SEQ ID NO: 1:
   (b) nucleotide #1108 to #1431 of SEQ ID NO: 10: and
   (c) naturally occurring allelic sequences and equivalent degenerative codon sequences of (a) and (b).

10. The method of claim 9, wherein said host cell is a mammalian cell and the DNA molecule further comprises a DNA sequence encoding a propeptide from a member of the TGF-β superfamily of proteins, said DNA sequence encoding a propeptide being linked in proper reading frame to the DNA coding sequence.

11. A purified bone morphogenetic protein-10 (BMP-10) polypeptide comprising the amino acid sequence from amino acid #1 to #108 as set forth in SEQ ID NO: 2.

12. A purified bone morphogenetic protein-10 (BMP-10) polypeptide comprising the amino acid sequence from amino acid #1 to #108 as set forth in SEQ ID NO: 11.

13. A purified BMP-10 polypeptide of claim 12 wherein said polypeptide is a dimer and wherein each subunit comprises the amino acid sequence from amino acid #1 to #108 of SEQ ID NO: 11.

14. A purified bone morphogenetic protein-10 (BMP-10) polypeptide produced by the steps of (a) culturing a cell transformed with a DNA molecule comprising the nucleotide sequence from nucleotide #779 to #1102 as shown in SEQ ID NO: 1; and (b) recovering and purifying from said culture medium a polypeptide comprising the amino acid sequence from amino acid #1 to amino acid #108 of SEQ ID NO: 2.

15. A purified bone morphogenetic protein-10 (BMP-10) polypeptide produced by the steps of (a) culturing a cell transformed with a DNA molecule comprising the nucleotide sequence from nucleotide #1108 to #1431 as shown in SEQ ID NO: 10; and (b) recovering and purifying from said culture medium a polypeptide comprising the amino acid sequence from amino acid #1 to amino acid #108 as shown in SEQ ID NO: 11.

16. A purified bone morphogenetic protein-10 (BMP-10) polypeptide according to claim 12, wherein said polypeptide is a dimer comprising two subunits, wherein one subunit comprises the amino acid sequence from amino acid #1 to amino acid #108 of SEQ ID NO: 11, and one subtrait comprises an amino acid sequence for a bone morphogenetic protein selected from the group consisting of BMP-1, BMP-2, BMP-3, BMP-4, BMP-5, BMP-6, BMP-7, BMP-8, BMP-9 and BMP-11.

17. A chimetic DNA molecule comprising a DNA sequence encoding a propeptide from a member of the TGF-$\beta$ superfamily of proteins linked in frame to a DNA sequence encoding a bone morphogenetic protein-10 (BMP-10) polypeptide, said BMP-10 polypeptide being selected from the group comprising amino acid #1 to #108 of SEQ ID NO: 2 and amino acid #1 to #108 of SEQ ID NO: 11.

* * * * *